United States Patent [19]
Dodge et al.

[11] Patent Number: 5,811,421
[45] Date of Patent: Sep. 22, 1998

[54] NAPHTHYL AND DIHYDRONAPHTHYL INTERMEDIATES, COMPOUNDS, COMPOSITIONS, AND METHODS

[75] Inventors: Jeffrey Alan Dodge; Kennan Joseph Fahey; Charles David Jones, all of Indianapolis; Charles Willis Lugar, III, McCordsville, all of Ind.

[73] Assignee: Eli Lilly and Company, Indianapolis, Ind.

[21] Appl. No.: 679,593

[22] Filed: Jul. 16, 1996

Related U.S. Application Data

[60] Provisional application No. 60/001,682 Jul. 31, 1995.

[51] Int. Cl.[6] ............... A61K 31/135; A61K 31/445; C07C 217/18; C07D 211/06
[52] U.S. Cl. ............... 514/212; 514/239.2; 514/319; 514/428; 514/51; 514/534; 514/546; 540/609; 544/171; 544/174; 546/205; 546/206; 548/576; 555/58; 560/108; 560/139; 564/324
[58] Field of Search .................... 546/205, 206; 514/319, 212, 239.2, 428, 648; 540/609; 544/174; 548/576; 564/324

[56] References Cited

U.S. PATENT DOCUMENTS

| | | | |
|---|---|---|---|
| 3,274,213 | 9/1966 | Lednicer | 260/326.5 |
| 3,293,263 | 12/1966 | Lednicer | 260/326.5 |
| 3,313,853 | 4/1967 | Lednicer | 260/570.7 |
| 3,320,271 | 5/1967 | Lednicer | 260/307 |
| 3,394,125 | 7/1968 | Crenshaw | 260/326.5 |
| 3,396,169 | 8/1968 | Lednicer | 260/294.7 |
| 3,413,305 | 11/1968 | Crenshaw | 260/326.5 |
| 3,483,293 | 12/1969 | Duncan et al. | 424/274 |
| 3,567,737 | 3/1971 | Lednicer | 260/326.5 |
| 3,862,232 | 1/1975 | Lednicer | 260/570.7 |
| 4,133,814 | 1/1979 | Jones et al. | 260/326.5 |
| 4,230,862 | 10/1980 | Suarez et al. | 546/237 |
| 4,380,635 | 4/1983 | Peters | 546/202 |
| 4,418,068 | 11/1983 | Jones | 424/267 |
| 4,859,695 | 8/1989 | McKissick | 514/408 |
| 4,910,212 | 3/1990 | Boyle et al. | 514/383 |
| 5,013,761 | 5/1991 | Beedle et al. | 514/650 |
| 5,254,568 | 10/1993 | Kapil et al. | 514/320 |
| 5,470,854 | 11/1995 | von Angerer | 514/233.5 |
| 5,472,962 | 12/1995 | Koizumi | 514/233.5 |
| 5,484,795 | 1/1996 | Bryant et al. | 514/319 |

FOREIGN PATENT DOCUMENTS

| | | |
|---|---|---|
| 0 124 369 | 11/1984 | European Pat. Off. |
| 0 516257A1 | 5/1992 | European Pat. Off. |
| 0703228A1 | 9/1995 | European Pat. Off. |
| 0731093 | 3/1996 | European Pat. Off. |
| WO 93/10113 | 5/1993 | WIPO |
| WO93/10741 | 6/1993 | WIPO |
| WO 95/10513 | 4/1995 | WIPO |

OTHER PUBLICATIONS

Jones, et al, "Antiestrogens 2. Structure–Activity Studies in a Series of 3–Aroyl–2–arylbenzo[b]thien Derivatives Leading to [6–Hydroxy–2(4–hydroxyphenyl) benzo[b]thien–3–yl][4–[2–(1–piperidinyl)ethoxy]phenyl]methanone Hydrochloride (LY156758), a Remarkably Effective Estrogen Antagonist with Only Minimal Intrinsic Estrogenicity", J. Med. Chem. vol. 27, 8, 1984, pp. 1057–1066.

J. Gubin, et al., "Recherche dans la serie des benzo[b]thiophenes IV. (Aminoalkloxy–4 benzoyl)–3 benzo[b]thiophenes a vocation antiangineuse", Eur. J. Med. Chem., vol. 10, 4, 1975 pp. 418–424.

Crenshaw, R.R., et al., *J. Med. Chem.*, 14(12):1185–1190 (1971).

Durani, N., et al., *Indian J. Chem.*, 22B:489–490 (1983).
Jones, C.D., et al., *J. Med. Chem.*, 35:931–938 (1992).
Lednicer, D., et al., *J. Med. Chem.*, 8:52–57 (1964).
Lednicer, D., et al., *J. Med. Chem.*, 9:172–175 (1965).
Lednicer, D., et al., *J. Med. Chem.*, 10:78–84 (1967).

*Primary Examiner*—Richard L. Raymond
*Attorney, Agent, or Firm*—Janelle D. Strode; David E. Boone

[57] ABSTRACT

The present invention provides compounds of formula

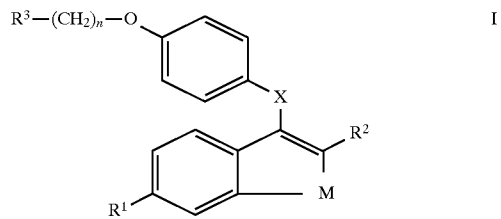

wherein $R^1$ is —H, —OH, —O($C_1$–$C_4$ alkyl), —OCO$C_6$H$_5$, —OCO($C_1$–$C_6$ alkyl), or —OSO$_2$($C_4$–$C_6$ alkyl);

$R^2$ is $C_1$–$C_6$ alkyl or $C_5$–$C_7$ cycloalkyl which is optionally substituted with 1 to 3 substitutents selected from the group consisting of $C_1$–$C_4$ alkyl, $C_1$–$C_4$ alkoxy, hydroxy, amino, nitro, and halo;

X is —CH(OH)— or —CH$_2$—;

M is —CH$_2$CH$_2$— or —CH═CH—;

n is 2 or 3; and $R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof. Also provided are methods of using the compounds of the present invention for the treatment of various medical indications associated with post-menopausal syndrome, uterine fibroid disease, endometriosis, and aortal smooth muscle cell proliferation. The present invention further provides pharmaceutical compositions of compounds of formula I, as well as intermediate compounds for the preparation thereof.

29 Claims, No Drawings

NAPHTHYL AND DIHYDRONAPHTHYL INTERMEDIATES, COMPOUNDS, COMPOSITIONS, AND METHODS

This application is based on Provisional application Ser. No. 60/001,682, filed Jul. 31, 1995.

FIELD OF THE INVENTION

This invention relates to the fields of pharmaceutical and organic chemistry and provides novel naphthyl and dihydronaphthyl compounds which are useful for the treatment of the various medical indications associated with post-menopausal syndrome, and uterine fibroid disease, endometriosis, and aortal smooth muscle cell proliferation, and pharmaceutical compositions thereof. The present invention further relates to intermediate compounds which are useful for preparing pharmaceutically active compounds of the present invention.

BACKGROUND OF THE INVENTION

"Post-menopausal syndrome" is a term used to describe various pathological conditions which frequently affect women who have entered into or completed the physiological metamorphosis known as menopause. Although numerous pathologies are contemplated by the use of this term, three major effects of post-menopausal syndrome are the source of the greatest long-term medical concern: osteoporosis, cardiovascular effects such as hyperlipidemia, and estrogen-dependent cancer, particularly breast and uterine cancer.

Osteoporosis describes a group of diseases which arise from diverse etiologies, but which are characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within 3 to 6 years after the cessation of mensus. This rapid loss is generally associated with an increase of bone resorption and formation. However, the resorptive cycle is more dominant and the result is a net loss of bone mass. Osteoporosis is a common and serious disease among post-menopausal women.

There are an estimated 25 million women in the United States, alone, who are afflicted with this disease. The results of osteoporosis are personally harmful and also account for a large economic loss due its chronicity and the need for extensive and long term support (hospitalization and nursing home care) from the disease sequelae. This is especially true in more elderly patients. Additionally, although osteoporosis is not generally thought of as a life threatening condition, a 20% to 30% mortality rate is related with hip fractures in elderly women. A large percentage of this mortality rate can be directly associated with post-menopausal osteoporosis.

The most vulnerable tissue in the bone to the effects of post-menopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the bio-mechanical strength of the overall structure. In post-menopausal osteoporosis, it is, primarily, the net resorption and loss of the trabeculae which leads to the failure and fracture of bone. In light of the loss of the trabeculae in post-menopausal women, it is not surprising that the most common fractures are those associated with bones which are highly dependent on trabecular support, e.g., the vertebrae, the neck of the weight bearing bones such as the femur and the fore-arm. Indeed, hip fracture, collies fractures, and vertebral crush fractures are hall-marks of post-menopausal osteoporosis.

At this time, the only generally accepted method for treatment of post-menopausal osteoporosis is estrogen replacement therapy. Although this therapy is generally successful, patient compliance with the therapy is low, primarily because estrogen treatment frequently produces undesirable side effects.

Throughout premenopausal time, most women have less incidence of cardiovascular disease than age-matched men. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that post-menopausal women having estrogen replacement therapy have a return of serum lipid levels to concentrations to those of the pre-menopausal state. Thus, estrogen would appear to be a reasonable treatment for this condition. However, the side-effects of estrogen replacement therapy are not acceptable to many women, thus limiting the use of this therapy. An ideal therapy for this condition would be an agent which would regulate the serum lipid level as does estrogen, but would be devoid of the side-effects and risks associated with estrogen therapy.

The third major pathology associated with post-menopausal syndrome is estrogen-dependent breast cancer and, to a lesser extent, estrogen-dependent cancers of other organs, particularly the uterus. Although such neoplasms are not solely limited to a post-menopausal women, they are more prevalent in the older, post-menopausal population. Current chemotherapy of these cancers has relied heavily on the use of anti-estrogen compounds such as, for example, tamoxifen. Although such mixed agonist-antagonists have beneficial effects in the treatment of these cancers, and the estrogenic side-effects are tolerable in acute life-threatening situations, they are not ideal. For example, these agents may have stimulatory effects on certain cancer cell populations in the uterus due to their estrogenic (agonist) properties and they may, therefore, be contraproductive in some cases. A better therapy for the treatment of these cancers would be an agent which is an anti-estrogen compound having negligible or no estrogen agonist properties on reproductive tissues.

In response to the clear need for new pharmaceutical agents which are capable of alleviating the symptoms of, inter alia, post-menopausal syndrome, the present invention provides new naphthalene and dihydronaphthylene compounds, pharmaceutical compositions thereof, and methods of using such compounds for the treatment of post-menopausal syndrome and other estrogen-related pathological conditions such as those mentioned below.

Uterine fibrosis (uterine fibroid disease) is an old and ever present clinical problem which goes under a variety of names, including uterine fibroid disease, uterine hypertrophy, uterine lieomyomata, myometrial hypertrophy, fibrosis uteri, and fibrotic metritis. Essentially, uterine fibrosis is a condition where there is an inappropriate deposition of fibroid tissue on the wall of the uterus.

This condition is a cause of dysmenorrhea and infertility in women. The exact cause of this condition is poorly understood but evidence suggests that it is an inappropriate response of fibroid tissue to estrogen. Such a condition has been produced in rabbits by daily administrations of estrogen for 3 months. In guinea pigs, the condition has been produced by daily administration of estrogen for four months. Further, in rats, estrogen causes similar hypertrophy.

The most common treatment of uterine fibrosis involves surgical procedures both costly and sometimes a source of complications such as the formation of abdominal adhesions and infections. In some patients, surgery is only a temporary treatment and the fibroids regrow. In those cases a hysterectomy is performed which effectively ends the fibroids but also the reproductive life of the patient. Also, gonadotropin releasing hormone antagonists may be administered, yet their use is tempered by the fact they can lead to osteoporosis. Thus, there exists a need for new methods for treating uterine fibrosis, and the methods of the present invention satisfy that need.

Endometriosis is a condition of severe dysmenorrhea, which is accompanied by severe pain, bleeding into the endometrial masses or peritoneal cavity and often leads to infertility. The cause of the symptoms of this condition appear to be ectopic endometrial growths which respond inappropriately to normal hormonal control and are located in inappropriate tissues. Because of the inappropriate locations for endometrial growth, the tissue seems to initiate local inflammatory-like responses causing macrophage infiltration and a cascade of events leading to initiation of the painful response. The exact etiology of this disease is not well understood and its treatment by hormonal therapy is diverse, poorly defined, and marked by numerous unwanted and perhaps dangerous side effects.

One of the treatments for this disease is the use of low dose estrogen to suppress endometrial growth through a negative feedback effect on central gonadotropin release and subsequent ovarian production of estrogen; however, it is sometimes necessary to use continuous estrogen to control the symptoms. This use of estrogen can often lead to undesirable side effects and even the risk of endometrial cancer.

Another treatment consists of continuous administration of progestins which induces amenorrhea and, by suppressing ovarian estrogen production, can cause regressions of the endometrial growths. The use of chronic progestin therapy is often accompanied by the unpleasant CNS side effects of progestins and often leads to infertility due to suppression of ovarian function.

A third treatment consists of the administration of weak androgens, which are effective in controlling the endometriosis; however, they induce severe masculinizing effects. Several of these treatments for endometriosis have also been implicated in causing a mild degree of bone loss with continued therapy. Therefore, new methods of treating endometriosis are desirable.

Smooth aortal muscle cell proliferation plays an important role in diseases such as atherosclerosis and restenosis. Vascular restenosis after percutaneous transluminal coronary angioplasty (PTCA) has been shown to be a tissue response characterized by an early and late phase. The early phase occurring hours to days after PTCA is due to thrombosis, with some vasospasms, while the late phase appears to be dominated by excessive proliferation and migration of aortal smooth muscle cells. In this disease, the increased cell motility and colonization by such muscle cells and macrophages contribute significantly to the pathogenesis of the disease. The excessive proliferation and migration of vascular aortal smooth muscle cells may be the primary mechanism to the reocclusion of coronary arteries following PTCA, atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., *Journal of the American College of Cardiology*, 8: 369–375 (Aug. 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See, "Prevention of Restenosis after Percutaneous Transluminal Coronary Angioplasty: The Search for a 'Magic Bullet'," Hermans et al., *American Heart Journal*, 1: 171–187 (July 1991).

In the pathogenesis of restenosis, excessive cell proliferation and migration occurs as a result of growth factors produced by cellular constituents in the blood and the damaged arterial vessel wall which mediate the proliferation of smooth muscle cells in vascular restenosis.

Agents that inhibit the proliferation and/or migration of smooth aortal muscle cells are useful in the treatment and prevention of restenosis. The present invention provides for the use of compounds as smooth aortal muscle cell proliferation inhibitors and, thus inhibitors of restenosis.

SUMMARY OF THE INVENTION

The present invention relates to compounds of formula I

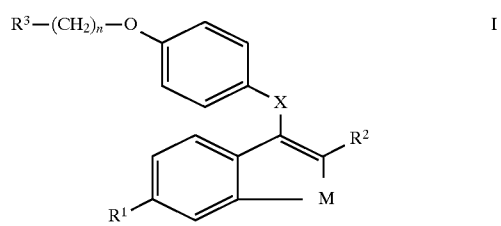

wherein $R^1$ is —H, —OH, —O($C_1$–$C_4$ alkyl), —OCOC$_6$H$_5$, —OCO($C_1$–$C_6$ alkyl), or —OSO$_2$($C_4$–$C_6$ alkyl);

$R^2$ is $C_1$–$C_6$ alkyl or $C_5$–$C_7$ cycloalkyl which is optionally substituted with 1 to 3 substitutents selected from the group consisting of $C_1$–$C_4$ alkyl, $C_1$–$C_4$ alkoxy, hydroxy, amino, nitro, and halo;

X is —CH(OH)— or —CH$_2$—;

M is —CH$_2$CH$_2$— or —CH═CH—;

n is 2 or 3; and $R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

Also provided by the present invention are intermediate compounds of formula IIIf

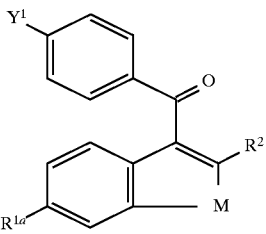

IIIf wherein $R^{1a}$ is —H, —OH, or —O($C_1$–$C_4$ alkyl);

$R^2$ is $C_1$–$C_6$ alkyl or $C_5$–$C_7$ cycloalkyl which is optionally substituted with 1 to 3 substitutents selected from the group consisting of $C_1$–$C_4$ alkyl, $C_1$–$C_4$ alkoxy, hydroxy, amino, nitro, and halo;

M is —$CH_2CH_2$— or —CH=CH—; and $Y^1$ is —OH, —$OCH_3$ or —O($CH_2$)$_n$-Z in which n is 2 or 3 and Z is a leaving group;

or a pharmaceutically acceptable salt thereof.

The present invention further relates to pharmaceutical compositions containing compounds of formula I, optionally containing estrogen or progestin and the use of such compounds, alone, or in combination with estrogen or progestin, for alleviating the symptoms of post-menopausal syndrome, particularly osteoporosis, cardiovascular related pathological conditions, and estrogen-dependent cancer. As used herein, the term "estrogen" includes steroidal compounds having estrogenic activity such as, for example, 17β-estradiol, estrone, conjugated estrogen (Premarin®), equine estrogen, 17β-ethynyl estradiol, and the like. As used herein, the term "progestin" includes compounds having progestational activity such as, for example, progesteone, norethylnodrel, nongestrel, megestrol, acetate, norethindrone, and the like.

DETAILED DESCRIPTION OF THE INVENTION

One aspect of the present invention includes compounds of formula I

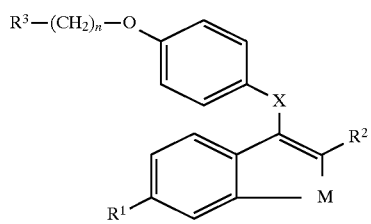

I wherein $R^1$ is —H, —OH, —O($C_1$–$C_4$ alkyl), —$OCOC_6H_5$, —OCO($C_1$–$C_6$ alkyl), or —$OSO_2$($C_4$–$C_6$ alkyl);

$R^2$ is $C_1$–$C_6$ alkyl or $C_5$–$C_7$ cycloalkyl which is optionally substituted with 1 to 3 substitutents selected from the group consisting of $C_1$–$C_4$ alkyl, $C_1$–$C_4$ alkoxy, hydroxy, amino, nitro, and halo;

X is —CH(OH)—, or —$CH_2$—;

M is —$CH_2CH_2$— or —CH=CH—;

n is 2 or 3; and $R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

General terms used in the description of compounds herein described bear their usual meanings. For example, "$C_1$–$C_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "$C_1$–$C_4$ alkoxy" represents a $C_1$–$C_4$ alkyl group attached through an oxygen such the like. Of these $C_1$–$C_4$ alkoxy groups, methoxy is highly preferred.

The starting material for one route of preparing compounds of the present invention, compounds of formula II below, are made essentially as described in U.S. Pat. No. 4,230,862, issued Oct. 28, 1980, which is herein incorporated by reference.

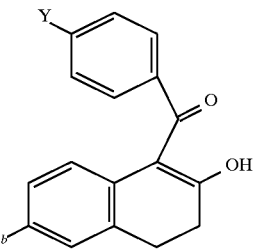

II wherein $R^{1b}$ is —H or —O($C_1$–$C_4$ alkyl); and

Y is methoxy or $R^3$—($CH_2$)$_n$—O—, in which $R^3$ and n are as defined above. Preferably, $R^{1b}$ is methoxy, Y is $R^3$—($CH_2$)$_n$—O—, $R^3$ is 1-piperidinyl, and n is 2.

In general, a tetralone which is readily available or is prepared via known procedures, or a salt thereof, of the formula

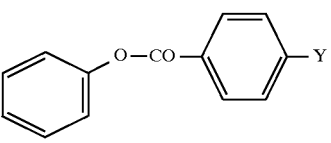

wherein $R^{1b}$ is as defined above, is reacted with an acylating agent such as a phenyl benzoate of the formula

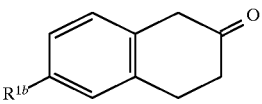

wherein Y is as defined above. The reaction generally is carried out in the presence of a moderately strong base such as sodium amide and is run at ambient temperature or below.

For the next step, one option allows for the selected formula II compound to be reacted, after conversion to an enol phosphate derivative, frequently generated in situ, under Grignard reaction conditions, with a Grignard reagent of the formula $R^2$-

wherein $R^2$ is $C_1$–$C_6$ alkyl or cycloalkyl, which is optionally substituted with 1 to 3 substituents selected from the group consisting of $C_1$–$C_4$ alkyl, $C_1$–$C_4$ alkoxy, hydroxy, amino, nitro, and halo, to provide compounds of formula IIIa, below, which also are known in the art (see, e.g. U.S. Pat. No. 4,230,862, supra). In the preparation of compounds of the present invention, the configuration of the $R^2$ substituent when $R^2$ is hydroxycyclohexyl, particularly 4-hydroxycyclohexyl, is trans. However, the stereoconfiguration will not be herein referred to throughout the present specification.

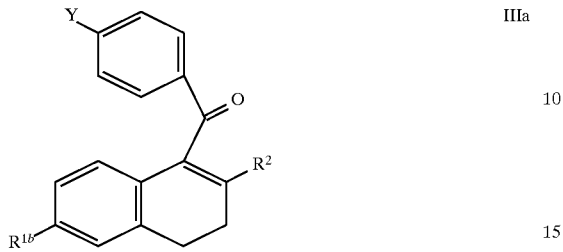

IIIa wherein $R^{1b}$, $R^2$, and Y are as defined above, or a pharmaceutically acceptable salt thereof. Alternatively, copper mediated chemistry may be employed to prepare compounds of formula IIIa by employing a cuprate reagent of the following formula:

$(R^2)_2CuLi$

Such reagents are known in the art and may be prepared by reacting the corresponding Grignard reagent with the appropriate copper species (such as CuBr-dimethyl sulfide complex).

Compounds of formula I in which M is —CH=CH— are prepared via the processes described below. However, when the preferred compounds of formula I are desired, in which M is —CH$_2$CH$_2$—, one of ordinary skill will recognize that aromatization may be completed at virtually any stage of the process herein described. Typically, a compound of formula IIIa will be aromatized using standard procedures. Generally, the desired dihydronaphthyl substrate is reacted with about 2 equivalents of 2,3-dichloro-5,6-dicyano-1,4-benzoquinone (DDQ) in the presence of an inert solvent or mixture of solvents such as, for example, dioxane, dichloromethane, toluene, dichloroethane, or benzene. The reaction mixture generally is heated to reflux for about 1 to 2 hours, and then allowed to stir at ambient temperature for a period from about 36 to about 72 hours.

When Y of a formula IIIa compound is $R^3$—(CH$_2$)$_n$—O—, such compounds can be reduced or deprotected as described infra. When Y of formula III compounds is methoxy (compounds of formula IIIb), one of the synthetic routes shown in Scheme I below is first utilized. In Scheme I, $R^{1b}$, $R^2$, $R^3$, M, and n are as defined above.

Scheme I

A

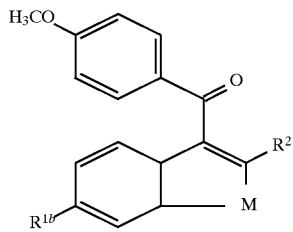

IIIb

↓

-continued

Scheme I

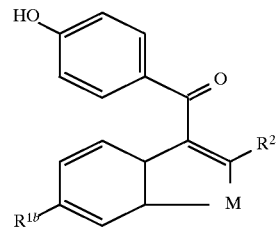

IIIc

↓

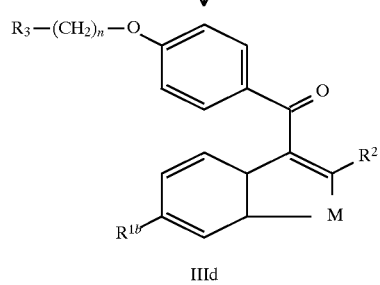

IIId

B

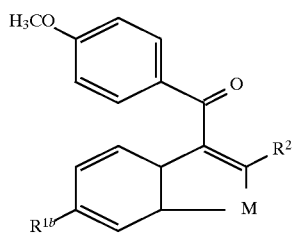

IIIb

↓

HO

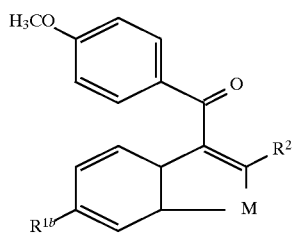

IIIc

↓

-continued
Scheme I

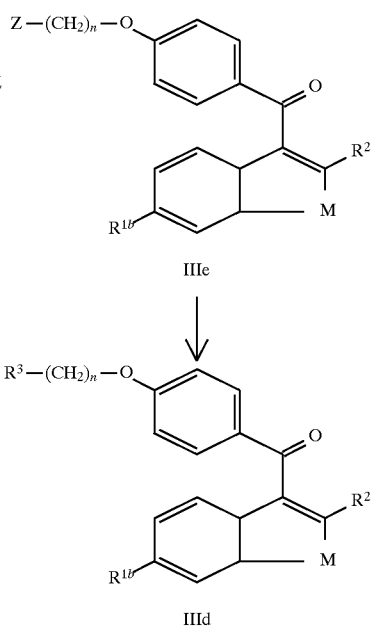

(in which Z is a leaving group)

IIIe

↓

IIId

Each step of synthetic routes A and B of Scheme I are carried out via procedures well known to one of ordinary skill in the art.

For example, compounds of formula IIIc are prepared by treating formula IIIb compounds with pyridine hydrochloride at reflux. Under these conditions, should $R^{1b}$ be alkoxy, this group will be dealkylated to a hydroxy group. Using this procedure will eliminate the deprotection step of such an alkoxy group at a later stage, if desired.

Alternatively, the Y methoxy group of formula IIIb can selectively be demethylated by treating the compound with an equivalent of sodium thioethoxide in an inert solvent such as N,N-dimethylformamide (DMF) at a moderately elevated temperature of about 80° C. to about 100° C. The progress of this step can be monitored via standard chromatographic techniques such as thin layer chromatography (TLC).

Once a formula IIIc compound is prepared, it can be reacted with a compound of the formula $R^3$—$(CH_2)_n$—Q 

wherein $R^3$ is as defined above and Q is a bromo or, preferably, a chloro moiety, to provide compounds of formula IIId. This reaction is shown as the last step of route A of Scheme I.

Under normal alkylation conditions, this reaction will be effected at each of the hydroxy groups which may be present in a formula IIIc molecule. However, selective alkylation at the 4-hydroxybenzoyl group can be achieved by carrying out the reaction in the presence of an excess of finely powdered potassium carbonate and using an equivalent to slight excess of the $R^3$—$(CH_2)_n$—Q reactant.

To prepare compounds of formula IIIe, as shown in route B of Scheme I, a formula IIIc compound is reacted with an excess of an alkylating agent of the formula Z—$(CH_2)_n$—Z' 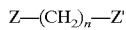

wherein Z and Z' each are the same or different leaving group, in an alkali solution.

Appropriate leaving groups include, for example, the sulfonates such as methanesulfonate, 4-bromosulfonate, toluenesulfonate, ethanesulfonate, isopropanesulfonate, 4-methoxybenzenesulfonate, 4-nitrobenzenesulfonate, 2-chlorobenzene sulfonate, and the like, halogens such as bromo, chloro, iodo, and the like, and other related groups. A preferred alkylating agent is 1,2-dibromoethane, and at least 2 equivalents, preferably, more than 2 equivalents, of 1,2-dibromoethane is used per equivalent of substrate.

A preferred alkali solution for this alkylation reaction contains potassium carbonate in an inert solvent such as, for example, methylethyl ketone (MEK) or N,N-dimethylformamide. In this solution, the 4-hydroxy group of the benzoyl moiety of a formula IIId compound is converted to a phenoxide ion which displaces one of the leaving groups of the alkylating agent.

This reaction is best run when the alkali solution containing the reactants and reagents is heated and allowed to run to completion. When using MEK as the preferred solvent, reaction times run from about 6 hours to about 20 hours.

The reaction product from this step, a compound of formula IIIe, is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, via standard techniques, to form compounds of formula IIId. Preferably, the hydrochloride salt of piperidine is reacted with the formula IIIe compound in an inert solvent, such as anhydrous N,N-dimethylformamide, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step can be monitored via standard chromatographic techniques.

Compounds of formula IIIe, IIIc, IIIc in which the 4-hydroxy group of the benzoyl moiety are deprotected are herein collectively depicted as compounds of formula IIIf, as shown below.

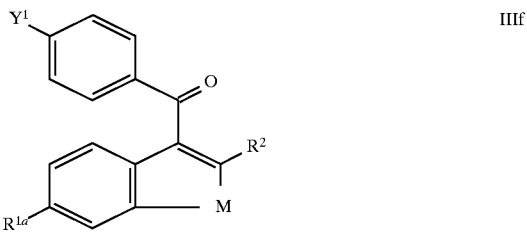

wherein $R^{1a}$ is —H, —OH, or —O($C_1$–$C_4$ alkyl);

$R^2$ is $C_1$–$C_6$ alkyl or $C_5$–$C_7$ cycloalkyl which is optionally substituted with 1 to 3 substituents selected from the group consisting of $C_1$–$C_4$ alkyl, $C_1$–$C_4$ alkoxy, hydroxy, amino, nitro, and halo;

M is —$CH_2CH_2$— or —CH=CH—; and $y^1$ is —OH, —$OCH_3$, or —O($CH_2$)$_n$—Z in which n is 2 or 3 and Z is a leaving group; or a pharmaceutically acceptable salt thereof.

Such formula IIIf compounds are novel and are useful as intermediates for preparing pharmaceutically active compounds of formula I of the present invention.

Compounds of formula IIId represent the starting material for one process for preparing pharmaceutically active compounds of formula Ia and Ib, as shown in Scheme II below.

Scheme II

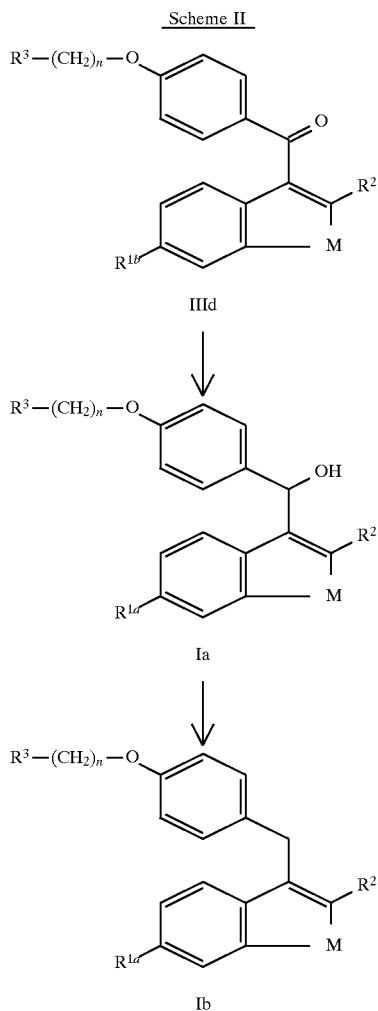

wherein $R^{1a}$, $R^{1b}$, $R^2$, $R^3$, M, and n are as defined above.

In Scheme II, a formula IIId compound, or a salt thereof, is added to an appropriate solvent and reacted with a reducing agent such as, for example, lithium aluminum hydride (LAH). Although the free base of a formula IIId compound may be used in this reaction, an acid addition salt, preferably the hydrochloride salt, is often more convenient.

The amount of reducing agent used in this reaction is an amount sufficient to reduce the carbonyl group of formula IIId compound to form the carbinol compounds of formula Ia, and to convert a salt of a formula IIId compound to a free base if a free base is not being employed. Generally, a liberal excess of the reducing agent per equivalent of the substrate is used.

Appropriate solvents include any solvent or mixture of solvents which will remain inert under reducing conditions. Suitable solvents include diethyl ether, dioxane, and tetrahydrofuran (THF). The anhydrous form of these solvents is preferred, and anhydrous tetrahydrofuran is especially preferred.

The temperature employed in this step is that which is sufficient to effect completion of the reduction reaction. Ambient temperature, in the range from about 17° C. to about 25° C., generally is adequate.

The length of time for this step is that amount necessary for the reaction to occur. Typically, this reaction takes from about 1 hour to about 20 hours. The optimal time can be determined by monitoring the progress of the reaction via conventional chromatographic techniques.

The carbinol products from this reaction step, optionally deprotected as described below, are novel and are useful for the methods described herein. One of ordinary skill in the art will recognize that the carbinol carbon is chiral. The present invention, therefore, contemplates the enantiomers of compounds of formula Ia, and compounds of formula I in which X is —CH(OH).

Once a carbinol of the present invention is prepared, such a compound is added to an inert solvent such as, for example, ethyl acetate, followed by the addition of a strong protic acid such as hydrochloric acid to provide novel compounds of formula Ib. This reaction typically is run at ambient temperature from about 17° C. to about 25° C., and generally only takes from about a few minutes to about 1 hour to complete. Crystallization of the final product is carried out through standard procedures.

Dealkylation/deprotection of a terminally-protected hydroxy group can be carried out prior to the preparation of formula Ia compounds, prior to the preparation of formula Ib compounds, or after protected compounds of formula Ib are prepared via procedures known to one of ordinary skill in the art. It is preferred, however, to dealkylate a protected formula Ib compound after its formation.

The reaction shown in Scheme II provides novel, pharmaceutically active compounds of formula Ia and Ib in which $R^{1a}$ is hydrogen, hydroxy or $C_1$–$C_4$ alkoxy and $R^2$ is $C_1$–$C_4$ alkyl or $C_5$–$C_7$ cycloalkyl which is optionally substituted with 1 to 3 substituents selected from the group consisting of $C_1$–$C_4$ alkyl, $C_1$–$C_4$ alkoxy, hydroxy, amino, nitro, and halo. Preferred formula Ia and Ib compounds are those in which $R^{1a}$ is methoxy or hydroxy, $R^2$ is cyclohexyl or cyclohexanol, $R^3$ is 1-piperidinyl, and n is 2. Of these, a formula Ia or Ib compound in which $R^{1a}$ is hydroxy, $R^2$ is cyclohexanol, $R^3$ is 1-piperidinyl, and n is 2 is especially preferred. These preferred compounds, as well as other formula Ia and Ib compounds, can be used as pharmaceutical agents or can be further derivitized to provide other formula I compounds which also are useful for practicing the methods of the present invention.

As an alternative to the reactions shown in Scheme II, a one-step process may be used to prepare formula Ib compounds of the present invention by reducing the respective ketone of formula III. More particularly, when $R^{1a}$ is —O($C_1$–$C_4$ alkyl), this hydroxy protecting group may be removed prior to using the present process, or optionally may be removed, in situ, following the present one-step reduction process. Additionally, the product from this process may be optionally salified via known procedures or as herein described.

In this process, a formula V compound

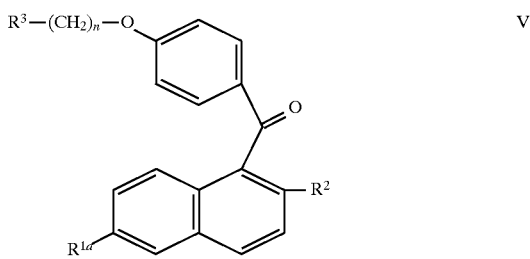

wherein $R^{1a}$, $R^2$, $R^3$, and n are as defined above, or a salt thereof, is reacted with a reducing agent such as lithium aluminum hydride or Red-Al®[sodium bis(2-methoxyethoxyl-aluminum hydride)] in the presence of a solvent having a boiling point in the range from about 160°

C. to about 200° C. When a compound of IIIc is used in the present process, upon completion, it is then alkylated with a compound of the formula

$$R^3-(CH_2)_n-Q$$

wherein $R^3$ is as defined above, via the above described procedures.

For the present reduction reaction, the amount of reducing agent used in this reaction is an amount sufficient to reduce the carbonyl group of a formula IIIc or IIId compound to form a compound of formula Ib. Generally, a liberal excess of the reducing agent per equivalent of the substrate is used.

The solvent used in the present process is required to have a relatively high boiling point, in the range from about 160° C. to about 200° C., as represented by solvents such as, for example n-propyl benzene, diglyme (1,1'-oxybis[2-methoxy-ethane]), and anisole. Of these, n-propyl benzene is the preferred solvent when preparing compounds of formula Ib when $R^{1a}$ is —$OCH_3$ and —$C_6H_4$-4'—$O(C_1-C_4$ alkyl). Red-Al, used as both a solvent and a reducing agent, is preferred when $R^{1a}$ is —OH.

The temperature used in this reaction is that which is sufficient to complete the reduction reaction. Preferably, the reaction mixture is heated to reflux for about 15 minutes to about 6 hours, allowed to cool to ambient temperature, and worked up via standard procedures [see, e.g., Fieser and Fieser, *Reagents for Organic Synthesis*, Vol. 1, page 584 (1968)] and as further described in the Examples herein. The optimal amount of time for this reaction to run, typically from about 10 minutes to about 1 hour, can be determined by monitoring the progress of the reaction via standard techniques.

The formula Ib products from the one-step reaction are extracted as described herein. Preferred formula Ib compounds from this reaction are the same as those preferred formula Ib compounds described above, and can be used as pharmaceutically active agents for the methods herein described, or can be derivatized to provide other novel compounds of formula I which also are useful for the present methods.

For example, when $R^1a$ is a $C_1$–$C_4$ alkyl hydroxy protecting group (thus, not having been dealkylated as one option in Scheme 1 provides), such groups can be removed via standard dealkylation techniques, as described in Example 6, infra, to prepare an especially preferred compound of formula Ib.

Other preferred compounds of formula I are prepared by replacing the newly formed $R^1$ of a formula Ib compound, or a formula Ia compound as described above, with a moiety of the formula —O—CO—($C_1$–$C_6$ alkyl), or —O—$SO_2$—($C_4$–$C_6$ alkyl) via well known procedures. See, e.g., U.S. Pat. No. 4,358,593.

For example, when an —O—CO($C_1$–$C_6$ alkyl) group is desired, the 6-hydroxy compound of formula Ia or Ib is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The acylation reactions which provide the aforementioned terminal $R^1$ groups of compounds of formula I are carried out at moderate temperatures in the range from about -25° C. to about 1000° C., frequently under an inert atmosphere such as nitrogen gas. However, ambient temperature is usually adequate for the reaction to proceed.

Such an acylation of this hydroxy group also may be performed by acid-catalyzed reactions of the appropriate carboxylic acids in inert organic solvents or heat. Acid catalysts such as sulfuric acid, polyphosphoric acid, methanesulfonic acid, and the like are used.

The aforementioned $R^1$ moiety of of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

Each of the above techniques which provide —O—CO—($C_1$–$C_6$ alkyl) moieties are carried out in solvents as discussed above. Those techniques which do not produce an acid product in the course of the reaction, of course, do not call for the use of an acid scavenger in the reaction mixture.

When a formula I compound is desired in which the $R^1a$ moiety of a formula Ia or Ib compound is converted to a group of the formula —O—$SO_2$—($C_4$–$C_6$ alkyl), a 6-hydroxy compound of formula Ia or Ib is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The 6-hydroxy compound also can be reacted with the appropriate sulfonic anhydride or mixed sulfonic anhydrides. Such reactions are carried out under conditions such as were explained above in the discussion of reaction with acid halides and the like.

Collectively, formula Ia and Ib compounds with their various defined substituents, and their derivatized compounds as described above, are represented as compounds of formula I of the present invention.

Although the free-base form of formula I compounds can be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxy-maleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethane-sulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The following examples are presented to further illustrate the preparation of compounds of the present invention. It is not intended that the invention be limited in scope by reason of any of the following examples.

NMR data for the following Examples were generated on a GE 300 MHz NMR instrument, and anhydrous d-6 DMSO was used as the solvent unless otherwise indicated.

PREPARATION 1

[3,4-Dihydro-2-hydroxyl-6-methoxynaphthalen-1-yl][4-[2-(1-piperdinyl)ethoxy]phenyl]methanone

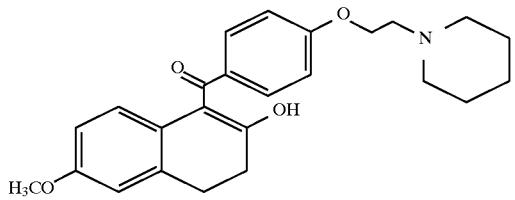

To a solution of 6-methoxy-2-tetralone (9.12 g, 51.7 mmol) stirring in tetrahydrofuran (100 mL) at −78° C. was added 4-[2-(-piperidinyl)ethoxy]benzoic acid hydrochloride salt (15.7 g, 51.7 mmol). To this mixture was added lithium hexamethyl-silazide (104 mL of a 1M solution in tetrahydrofuran, 103.51 mmol) at a rate such to maintain the temperature below −65° C. The reaction was stirred at −78° C. for 1 hour then quenched with saturated aqueous ammonium chloride. After removal of the tetrahydrofuran in vacuo, ethyl ether was added and resulting mixture was extracted consecutively with aqueous solutions of sodium hydroxide. The aqueous was acidified with hydrochloric acid. The acidic extract was made basic by addition of saturated aqueous sodium bicarbonate then washed with Et$_2$O. The combined organic extracts were dried (sodium sulfate), filtered, and concentrated to give 4.0 g (19%) of the desired product as a dark yellow oil: $^1$H NMR (300 MHz, CDCl$_3$) δ 1.44 (m, 2H), 1.61 (m, 4H), 2.50 (m, 4H), 2.58 (t, J=6.6, 7.1, 2H), 2.77 (t, J=6.1, 6.0, 2H), 2.92 (t, J=7.1, 6.7, 2H), 3.76 (s, 3H), 4.12 (t, J=6.0, 6.0, 2H), 6.44 (dd, J=2.7, 8.6, 1H), 6.64 (d, J=8.7, 1H), 6.71 (d, J=2.6, 1H), 6.80 (d, J=7.1, 2H), 7.48 (d, J=7.0, 2H). EA calc'd for C 73.68, H 7.17, N 3.44. found C 73.13, H 7.22, N 3.39; MS (FD) m/e 407 (M+); IR 1605.94 cm$^{-1}$.

PREPARATION 2

[3,4-Dihydro-2-ethyl-6-methoxynaphthalen-1-yl][4-[2-(1-piperdinyl)ethoxy]phenyl]methanone

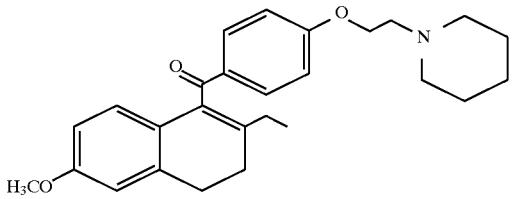

To a suspension of sodium hydride (0.60 g of a 60% oil dispersion, 15.1 mmol) stirring at tetrahydrofuran (50 mL) at 0° C. was added a mixture of diphenylchlorophosphate (3.30 mL, 15.1 mmol) and the product of Preparation 1 (5.6 g, 13.72 mmol) in tetrahydrofuran (50 mL). After 2.5 hours, the resulting solution was quenched with saturated aqueous ammonium chloride. The reaction mixture was diluted with ethyl acetate and extracted consecutively with saturated aqueous solutions of ammonium chloride, sodium hydroxide, and sodium chloride. The organic extracts were dried (sodium sulfate) and filtered. Concentration afforded a dark oil which was dissolved in tetrahydrofuran (150 mL). This solution was cooled to -780° C. and copper bromide-dimethylsulfide complex (4.34 g, 21.1 mmol) was added followed by ethyl magnesium bromide (7.0 mL of a 3,0M solution, 21.1 mmol). Additional equivalents of copper bromide dimethyl sulfide complex and ethyl magnesium bromide were added as necessary. After complete consumption of the enol phosphate intermediate, the reaction was warmed to −30° C. and quenched with saturated aqueous ammonium chloride. The mixture was then extracted with ethyl acetate and the combined organic extracts washed with saturated aqueous ammonium chloride, 1N aqueous sodium hydroxide, and brine. The resulting dark oil was purified by flash chromatography (silica gel, chloroform to 5% methanol/chloroform gradient) to give 3.48 g (60%) of the desired product as a dark yellow oil: $^1$H NMR (300 MHz, CDCl$_3$) δ 0.98 (t, J=7.5, 7.5, 3H), 1.43–1.56, (m, 2H), 1.58–1.63 (m, 4H), 2.08 (q, J=, 2H), 2.37 (t, J=7.6, 8.3, 2H), 2.49 (m, 4H), 2.78 (t, J=6.0, 5.9, 2H), 2.88 (t, J=8.2, 7.6, 2H), 3.75 (s, 3H), 4.15 (t, J=6.0, 6.0, 2H), 6.53 (dd, J=2.7, 8.5, 1H), 6.68 (d, J=8.4, 1H), 6.72 (d, J=2.4, 1H), 6.88 (d, J=8.8, 2H), 7.93 (d, J=8.7, 2H); EA calc'd C 77.29, H 7.93, N 3.34, found C 77.15, H 8.18, N 3.32; MS (FD) m/e 419 (M+);IR (chloroform) 1653.21 cm$^{-1}$.

PREPARATION 3

[3,4-Dihydro-2-(4-tert-butyldimethylsilyloxycyclohexyl)-6-methoxynaphthalen-1-yl][4-[2-(1-piperdinyl)ethoxy]phenyl]methanone

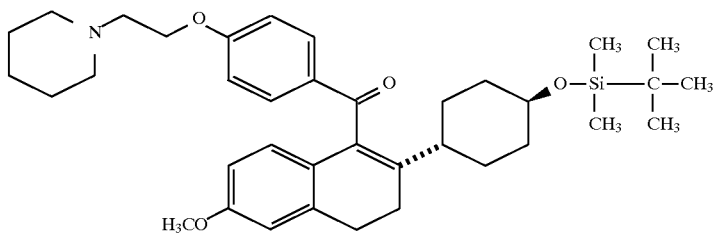

Prepared in the same manner as the product of Preparation 2 using a stock solution of the product of Preparation 1 (13.06 g, 20.42 mmol), copper bromide-dimethylsulfide complex (12.59 g, 61.26 mmol), trans-4-t-butyldimethylsilyoxycyclo-hexylmagnesium bromide [prepared by adding trans-4-t-butyldimethylsiloxy-bromocyclohexane to a suspension of magnesium filings (3.00 g, 123 mmol) in anyhydrous tetrahydrofuran (150 mL) in tetrahydrofuran (150 ml) The mixture was allowed to exotherm to reflux and subsequently stirred for 4 hours]. This provided 4.6 g (37%) of the desired product as a dark yellow oil. MS (FD) m/e-603 (M+).

PREPARATION 4

[3,4-Dihydro-2-hexyl-6-methoxynaphthalen-1-yl][4-[2-(1-piperdinyl)ethoxy]phenyl]methanone

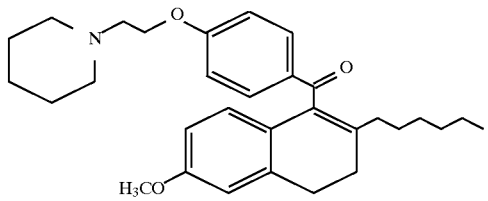

Synthesized in the same manner as shown in Preparation 2 using a stock solution of the product of Preparation 1 (13.0 g, 20.42 mmol), copper bromide-dimethylsulfide complex (12.59 g, 61.26 mmol), 1-hexyl magnesium bromide solution [prepared in the same manner as the Grignard reagent described in Preparation 3 using magnesium turnings (3.00 g, 123 mmol), 1-bromo-n-hexane (8.6 ml, 61.26 mmol), and 150 ml anhydrous tetrahydrofuran] to yield 3.5 g (36%) of the desired product as a dark yellow oil. MS (FD) m/e 475 (M+).

PREPARATION 5

[3,4-Dihydro-2-ethyl-6-hydroxynaphthalen-1-yl][4-[2-(1-piperdinyl)ethoxy]phenyl]methanone

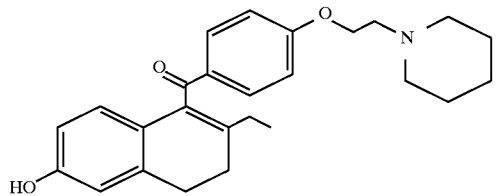

To a solution of the product of Preparation 2 (3.40 g, 8.10 mmol) stirring in methylene chloride (200 mL) at ambient temperature was added ethanethiol (3.00 mL, 40.5 mmol) followed by aluminum chloride (5.40 g, 40.5 mmol). After stirring vigorously for 0.5 hours, the dark red solution was quenched with saturated aqueous sodium bicarbonate. The resulting mixture was extracted with saturated aqueous sodium bicarbonate and brine. The organic extract was dried (sodium sulfate), filtered, and concentrated. The resulting dark oil was purified by flash chromatography (silica gel, 2% to 5% MeOH/CHCl$_3$ gradient) to give 2.00 g (61%) of the desired product as a yellow foam: $^1$H NMR (300 MHz, CDCl$_3$) δ 0.97 (t, J=7.5, 7.4, 3H), 1.42–1.47 (m, 2H), 1.63 (m, 4H), 2.07 (q, J=, 2H), 2.35 (t, J=8.6, 8.2, 2H), 2.54 (m, 4H), 2.80 (m, 4H), 4.12, (t, J=5.8, 5.7, 2H), 6.42 (dd, J=2.5, 7.3, 1H) 6.60 (m, 2H) 6.76 (d, J=8.8, 2H), 7.87 (d, J=8.7, 2H); MS (FD) m/e 405 (M+); IR (CHCl$_3$) 1653, 3597.70 cm$^{-1}$.

PREPARATION 6

[3,4-Dihydro-2-(4-trans-hydroxycyclohexyl)-6-hydroxynaphthalen-1-yl][4-[2-(1-piperdinyl)ethoxy]phenyl]methanone hydrochloride

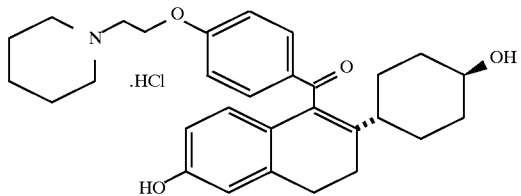

Prepared in the same manner as shown in Preparation 5 using the product of Preparation 3 (4.5 g, 7.46 mmol), aluminum chloride (8.6 g, 64.4 mmol) aluminum chloride, ethanethiol (3.4 ml, 46.0 mmol), in dichloromethane (200 ml) to yield 1.9 g (54%) of the desired product as a light yellow foam: EA calc'd C 75.76, H 7.84, N 2,94, found C 75.51, H 7.79, N 2.97. MS (FD) m/e 475 (M+); IR-1653.21 cm$^-$;. $^1$H NMR (300 MHz,CDCl$_3$) δ 1.20–1.24 (m, 2H), 1.57–1.76 (m, 8H), 2.03–2.18 (m, 2H), 2.25–2.30 (m, 1H), 2.37 (t, J=7.5, 7.6, 2H), 2.64–2.70 (m, 4H), 2.83–2.94 (m, 5H), 3.59–3.64 (m, 2H), 4.25 (t, J=5.6, 5.6, 2H), 6.51 (dd, J=8.3, 2.5, 2.5, 1H), 6.67 (d, J=8.3, 1H), 6.70 (d, J=2.3, 1H), 6.85 (d, J=8.8, 2H), 7.97 (d, J=8.6, 2H)

PREPARATION 7

[3,4-Dihydro-2-hexyl-6-hydroxynaphthalen-1-yl][4-[2-(1-piperdinyl)ethoxy]phenyl]methanone hydrochloride

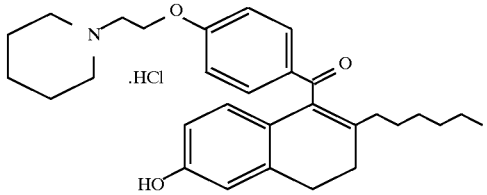

Prepared in the same manner as shown in Preparation 1 using the product of Preparation 4 (3.4 g, 7.15 mmol), aluminum chloride (4.8 g, 35.79 mmol), ethanethiol (2.7 ml, 35.79 mmol), and dichloromethane (200 mL) to yield 0.25 g (8%) of the desired product as a yellow foam: $^1$H NMR (300 MHz, CDCl$_3$) δ 0.92 (t, J=6.4, 6.3, 3H), 1.27–1.38 (m, 6H), 1.47–1.58 (m, 4H), 1.73–1.77 (m, 4H), 2.16 (t, J=8.2, 7.2), 2.44 (t, J=7.5, 8.2), 2.69–2.76 (m, 4H), 2.88–2.97 (m, 4H), 4.25 (t, J=5.8, 5.6, 2H), 6.53 (dd, J=8.2, 2.5, 2.4, 1H), 6.67, (d, J=8.3, 1H), 6.73 (d, J=2.2, 1H), 6.86 (d, J=8.7, 2H), 7.38 (s, 1H), 7.97 (d, J=8.6, 2H); IR (CDCl$_3$) 1600; MS (FD) m/e 461 (M+).

EXAMPLE 1

[2-Ethyl-6-hydroxynaphthalen-1-yl][4-[2-(1-piperdinyl)ethoxy]phenyl]methane hydrochloride

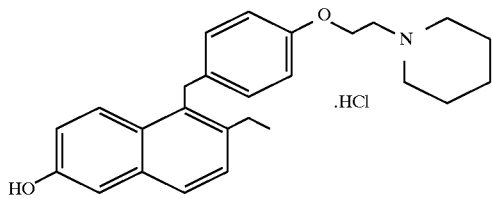

To a solution of the product of Preparation 5 (2.00 g, 4.93 mmol) stirring in tetrahydrofuran (100 mL) at 0° C. was slowly added lithium aluminum hydride (10.4 mL of a 1.0M solution in tetrahydrofuran, 10.4 mmol). The reaction was warmed to ambient temperature, stirred for 2 hours, then quenched with saturated aqueous sodium potassium tartate. After addition of ethyl acetate, the organic extract was washed with saturated aqueous sodium potassium tartate, water, and brine. The organic extract was dried (sodium sulfate), filtered, and concentrated to afford the carbinol as a white foam which was carried on without further purification. Thus, the foam was dissolved in ethyl acetate and the solution subsequently saturated with hydrochloric acid gas. After 18 hours at ambient temperature, the mixture was quenched with saturated aqueous sodium bicarbonate. The layers were separated and the organic extract dried (sodium sulfate), filtered, and concentrated. The resulting yellow foam was purified by flash chromatography (silica gel, 2 to 10% MeOH/CHCl$_3$ gradient) to give 0.91 g (47%) of the desired product as a yellow foam: $^1$H NMR (300 MHz, CDCl$_3$) δ 1.81 (t, J=7.5, 7.5, 3H), 1.45 (m, 2H), 1.64 (m, 4H), 2.58 (m, 4H), 2.79 (m, 4H), 4.04 (t, J=6.0, 6.0, 2H), 4.36 (s, 2H), 6.65 (d, J=8.6, 2H), 6.88 (d, J=8.6, 2H), 6.96 (dd, J=2.6, 9.2, 1H), 7.07 (d, J=2.6, 1H), 7.30 (d, J=8.5, 1H), 7.53 (d, J=8.5, 1H), 7.73 (J=9.1, 1H); EA calc'd for C 80.17, H 8.02, N 3.60. found C 80.18, H 8.02, N 3.54; MS (FD) m/e 390 (M+); IR (CHCl$_3$) 1510, 3597 cm$^{-1}$.

EXAMPLE 2

[2-(4-cyclohexyl)-6-hydroxynaphthalen-1-yl][4-[2-(1-piperdinyl)ethoxy]phenyl]methane hydrochloride

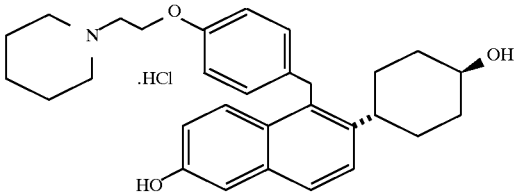

Prepared in the same manner as shown in Example 1 using the product of Preparation 6 (1.1 g, 2.31 mmol), lithium aluminum hydride (9.2 ml of a 1M solution in tetrahydrofuran, 9.2 mmol), and anydrous tetrahydrofuran (100 ml). Acidification of the crude reaction product (100 ml 1N HCl1/100 ml tetrahydrofuran) gave 0.3 g (34%) of the desired product as a light brown solid: MS (FD) m/e 460 (M+); IR 3163.66 cm$^{-1}$; $^1$H NMR (300 MHz,DMSO-—d$_6$) δ 1.15–1.21 (m, 2H) , 1.29–1.59 (m, 10H), 1.82–1.87 (m, 2H), 2.46–2.54 (m, 4H), 2.57 (t, J=5.8, 5.7, 2H), 2.85–2.90 (m, 1H), 3.13 (d, J=4.8, 1H), 3.93 (t, J=5.9, 5.9, 2H), 4.31 (s, 2H), 4.52 (d, J=4.3, 1H), 6.75 (d, J=8.6, 2H), 6.89–7.02 (m, 4H), 7.33 (d, J=8.7, 1H), 7.53 (d, J=8.7, 1H), 7.77 (d, J=9.2, 1H), 9.57 (s, 1H).

EXAMPLE 3

[2-(1-Hexyl)-6-hydroxynaphthalen-1-yl][4-[2-(1-piperdinyl)ethoxy]phenyl]methane hydrochloride

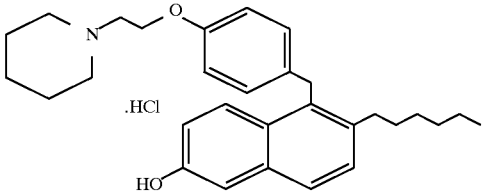

Prepared in the same manner as shown for Example 1 using the product of Preparation 7 (1.1 g, 2.39 mmol), lithium aluminum hydride (7.2 ml of a 1.0M solution in tetrahydrofuran, 7.2 mmol), and tetrahydrofuran (150 ml). Acidification of the crude reaction mixture (100 ml 1N HCl/100 ml tetrahydro-furan) gave 0.10 g (9%) of the desired product as a light yellow foam: $^1$H NMR (300 MHz,CDCl$_3$) δ 0.97 (t, J=6.7, 6.7, 3H), 1.31–1.80 (m, 14H), 2.69–2.96 (m, 8H), 4.16 (t, J=5.9, 5.8, 2H), 4.47 (s, 2H), 6.76 (d, J=8.6, 2H), 7.00 (d, J=8.5, 2H), 7.07 (dd, J=9.0, 2.5, 2.5, 1H), 7.19 (d, J=2.6, 1H), 7.39 (d, J=8.7, 1H), 7.63 (d, J=8.4, 1H), 7.85 (d, J=9.2, 1H).

PREPARATION 8

[3,4-Dihydro-2-cyclohexyl-6-methoxynaphthalen-1-yl][4-[methoxyphenyl]]methanone

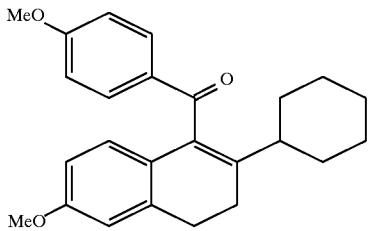

To as suspension of sodium hydride (1.48 g of a 60% dispersion in mineral oil, 36.9 mmol) stirring in tetrahydrofuran (100 mL) at 0° C. was slowly added a solution of diphenylchlorophosphate (7.65 g, 36.9 mmol) and the product of Preparation 1 (10.4 g, 33.5 mmol) in tetrahydrofuran (100 mL). After 1.5 hours, additional diphenylchlorophosphate (5 mL) was added and the reaction allowed to proceed for 2.5 hours then quenched with saturated aqueous ammonium chloride. The resulting mixture was extracted with ethyl acetate and the combined organic extracts washed with saturated aqueous ammonium chloride then brine. The organic extract was dried (sodium sulfate), filtered, and concentrated. The resulting yellow oil was purified by flash chromatography (silica gel, 20–35% ethyl acetate/hexane gradient) to give 11.2 g of the enol phosphate as a yellow oil which was employed in the subsequent step without further purification. Thus, the crude enol phosphate was dissolved in tetrahydrofuran (150 mL) and cooled to −78° C. To this stirred solution was added copper bromide-dimethlysulfide complex (4.20 g, 20.46 mmol) followed by cyclohexyl magnesium bromide (10.2 mL of a 2.0M solution in tetrahydrofuran, 5.1 mmol). After 2 hours, additional cyclohexyl magnesium bromide (5 mL) was added. The resulting solution was allowed to stir at −78° C. for 1 hour, then warmed to −20° C. and subsequently quenched with a solution of saturated aqueous ammonium chloride. The mixture was extracted with ethyl acetate and the organic extract washed with saturated aqueous ammonium chloride and brine. The organic portion was dried (sodium sulfate), filtered, and concentrated. The resulting oil was purified by flash chromatography (silica gel, 100% hexanes to 10% ethyl acetate/hexane gradient) to give a mixture of the desired product along with phenol. This material was dissolved in ethyl ether and extracted with 1N aqueous sodium hydroxide. The organic extract was dried (sodium sulfate), filtered, and concentrated to yield 3.25 g (26%) of the desired product as a yellow oil: $^1$H NMR (300 MHz CDCl$_3$) δ 1.08 (m, 2H), 1.32–1.37 (m, 2H), 1.51–1.64 (m, 6H), 2.20 (m, 1H), 2.33 (t, J=8.1, 7.5, 2H), 2.83 (t, J=8.0, 7.6, 2H), 3.75 (s, 3H), 3.85 (s, 3H), 6.53 (dd, J=2.7, 8.5, 1H), 6.67 (d, J=8.4, 1H), 6.72 (d, J=2.5, 1H) 6.90 (d, J=8.7, 2H), 7.95 (d, J=8.8, 2H); MS (FD) m/e 376 (M+); IR (CHCl$_3$) 1654.17 cm$^{-1}$.

PREPARATION 9

[3,4-Dihydro-2-cyclohexyl-6-methoxynaphthalen-1-yl][4-[hydroxyphenyl]]methanone

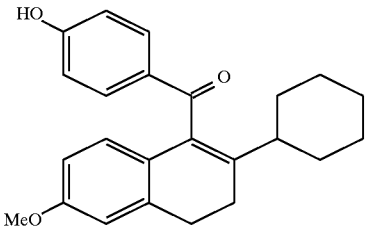

To a solution of ethanethiol (0.91 mL, 12.4 mmol) stirring in Et$_2$O (30 mL) at 0° C. was added n-BuLi (6.70 mL of a 1.6M in hexanes, 10.72 mmol) dropwise. After 0.5 hours, the mixture was concentrated to dryness. To this white solid was added a solution of the product of Preparation 8 (3.10 g, 8.24 mmol) in N,N-dimethylformamide (30 mL) and the resulting mixture heated to 90° C. After 4 hours, the mixture was cooled to ambient temperature, quenched with saturated aqueous ammonium chloride, and concentrated. The resulting material was dissolved in ethyl acetate and extracted with saturated aqueous ammonium chloride. The organic portion was dried (sodium sulfate), filtered, and concentrated. The resulting oil was purified by flash chromatography (silca gel, 10%–30% ethyl acetate/hexane gradient) to give 1.56 g (81% yield based on unrecovered starting material) of the desired phenol as a yellow oil: $^1$H NMR (300 MHz, CDCl$_3$) δ 1.06–1.68 (m, 10H), 2.20 (m, 1H), 2.37 (t, J=7.3, 8.4, 2H), 2.83 (t, J=8.0, 7.7, 2H) 3.75 (s, 3H), 6.54 (dd, J=2.7, 1H), 2.68 (d, J=8.5, 1H), 6.72 (d, J=2.7, 1H), 6.82 (d, J=8.7, 2H), 7.91 (d, J=8.6, 2H); ; MS (FD) m/e 362 (M+); IR (CDCl$_3$) 1651.28 cm$^{-1}$.

EXAMPLE 4

[3,4-Dihydro-2-cyclohexyl-6-methoxynaphthalen-1-yl][4-[2-(1-piperdinyl)ethoxy]phenyl]methanone

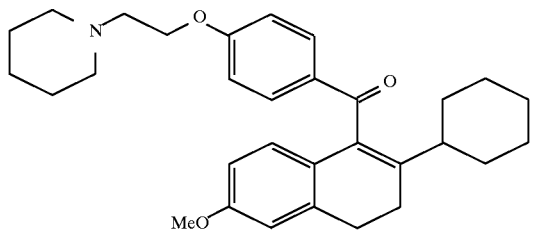

To a solution of the product of Preparation 9 (1.93 g, 5.32 mmol) stirring in N,N-dimethylformamide (40 mL) at ambient temperature was added N-(chloroethyl)piperidine hydrochloride (0.98 g, 5.32 mmol) followed by anhydrous potassium carbonate (3.68 g, 26.60 mmol). After 18 hours, ethyl acetate was added and the reaction was extracted with water then brine. The organic extract was dried (sodium sulfate), filtered, and concentrated. The resulting brown oil was purified by flash chromatography (150 g silica gel, CHCl$_3$ to 5% MeOH/CHCl$_3$ gradient) to yield 2.40 g (95%) of the desired product as an orange foam: $^1$H-NMR (300 MHz, CDCl$_3$) δ 1.08 (m, 2H), 1.32–1.65 (m, 14H), 2.19 (m, 1H), 2.33 (t, J=7.5, 8.1, 2H), 2.51 (m, 4H), 2.77–2.85 (m, 4H), 3.75 (s, 3H), 4.15 (t, J=6.0, 5.9, 2H), 6.55 (dd, J=2.7, 8.5, 1H), 6.67 (d, J=8.5, 1H), 6.71 (d, J=2.5, 1H), 6.88 (d, J=8.7, 2H), 7.93 (d, J=8.7, 2H); MS (FD) m/e 474 (M+); IR (CDCl$_3$) 1653 cm$^{-1}$.

EXAMPLE 5

[2-Cyclohexyl-6-methoxynaphthalen-1-yl][4-[2-(1-piperdinyl)ethoxy]phenyl]methane

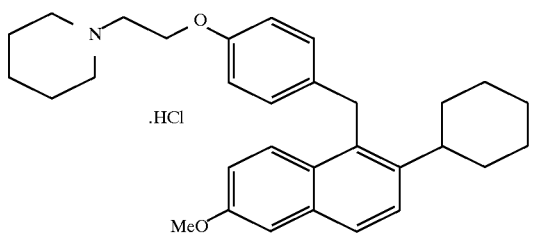

To a solution of the product of Example 4 (2.10 g, 4.44 mmol) stirring in tetrahydrofuran (50 mL) at 0° C. was added lithium aluminum hydride (8.9 mL of a 1.0M solution in tetrahydrofuran, 8.9 mmol). After 1.5 hours, the reaction was carefully quenched with saturated aqueous sodium potassium tartrate followed by addition of ethyl acetate. The resulting mixture was extracted with saturated aqueous sodium potassium tartrate then brine. The organic extract was dried (sodium sulfate), filtered, and concentrated. The resulting oil was dissolved in ethyl acetate (100 mL) and this solution was saturated with hydrochloric acid gas then stirred at ambient temperature for 45 minutes before quenching with saturated aqueous sodium bicarbonate. This solution was extracted with saturated aqueous sodium bicarbonate, dried (sodium sulfate), filtered, and concentrated. The resulting material was purified by flash chromatography (200 g silica gel, 5% MeOH/CHCl₃) to give a yellow foam which was used without further purification. Thus, the crude reaction product was dissolved in dissolved in ethyl ether and this solution saturated with hydrochloric acid gas. After 0.5 hours, the mixture was concentrated to yield 1.73 g (85%) of the desired product as a thick oil: $^1$H NMR (300 MHz, CDCl₃) δ 1.31–2.76 (m, 16H), 2.74 (t, J=6.1, 6.1, 2H), 2.93 (m, 4H), 3.90 (s, 3H), 4.04 (t, J=6.1, 6.1, 2H), 4.42 (s, 2H), 6.76 (d, J=8.6, 2H), 6.96 (d, J=8.6, 2H), 7.05 (dd, J=2.6, 9.2, 1H), 7.11 (d, J=2.7, 1H), 7.46 (d, J=8.6, 1H)7.66 (d, J=8.6, 1H), 7.83 (d, J=9.2, 1H).EA calc'd for C 75.36, H 8.16, N 2.84; found C 75.57, H 7.99, N 2.63; MS (FD) m/e 457 (M+-HCl); IR (CHCl₃) 1628.23 cm$^{-1}$.

EXAMPLE 6

[2-Cyclohexyl-6-hydroxynaphthalen-1-yl][4-[2-(1-piperdinyl)ethoxy]phenyl]methane hydrochloride

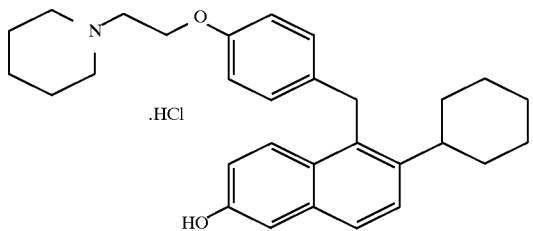

In a re-sealable reaction vessel, a chilled (0° C.) solution of the product of Example 5 (0.50 g, 1.01 mmol) in dichloroethane (10 mL) was saturated with boron trichloride gas. The reaction vessel was sealed and the mixture warmed to ambient temperature. After 6.5 hours, the solution was carefully quenched with methanol then diluted with ethyl acetate. The organic portion was extracted with saturated aqueous sodium bicarbonate, brine, dried (sodium sulfate), filtered, and concentrated. The resulting oil was purified by flash chromatography (50 g silica gel, 2% MeOH/CHCl₃) and the hydrochloride salt was prepared as in Example 5 to yield 0.10 g (35% yield based on unrecovered starting material): $^1$H NMR (300 MHz, CDCl₃) δ 1.27–1.81 (m, 16H), 2.50 (m, 4H), 2.79 (t, J=5.5, 5.7, 2H), 2.90 (m, 1H), 4.05 (t, J=5.9, 5.8, 2H), 4.38 (s, 2H), 6.67 (d, J=8.5, 2H), 6.91 (d, J=8.5, 2H), 6.96 (dd, J=2.7, 9.2, 1H), 7.07 (d, J=2.5, 1H), 7.41 (d, J=8.7, 1H), 7.56 (d, J=8.7, 1H), 7.78 (d, J=9.06, 1H); EA calc'd for C 81.27, H 8.41, N 3.16; found C 80.57, H 8.10, N 3.47; MS (FD) m/e 444 (M+).

PREPARATION 10

[3, 4-Dihydro-2-cyclohexyl-6-hydroxy-naphthalen-1-yl][4-[2-(1-piperidinyl)ethoxy]phenyl]methanone

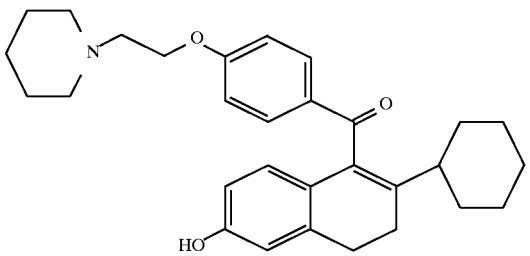

Prepared in the same manner as shown in Preparation 5 using the product of Example 4 (7.7 g, 16.3 mmol), aluminum chloride (10.8 g, 81.3 mmol) and ehtnaethiol (6.0 mL, 81.3 mmol) in dichloromethane (200 mL) to provide 1.35 g of the desired material as a tan solid: EA calc'd C 78.4, H 8.11, N 3.05, found C 78.90, H 7.38, N. 2.83, MS (FD) 459 (M+); IR (kBr) 3347, 1598 cm$^{-1}$; H NMR (CDCl₃) 7.99 (d, J=9 Hz, ZH), 6.80 (d, J=9 Hz, ZH), 6.70 (d, J=2 Hz, 1H), 6.65 (d, J=9 Hz, 1H), 6.50 (dd, J=9.3 Hz, 2H), 4.20 (t, J=6.1 Hz, ZH, 2.2–3.0 (series of M, 7H), 1–1.8 (series of m 16H).

EXAMPLE 7

[3, 4-Dihydro-2-cyclohexyl-6-hydroxy-naphthalen-1-yl][4-[2-(1-piperidinyl)ethoxy]phenyl]methanol

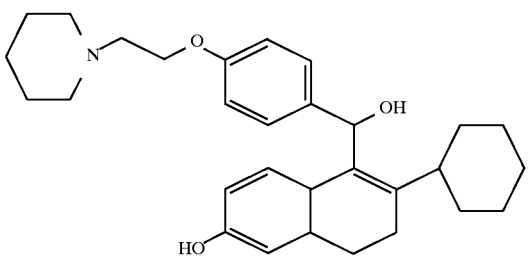

To a solution of the product of Preparation 10 (30 mg, 0.6 mmol) stirring tetrahydrofuran (5 ml) at 0° C. was added lithium aluminum hydride (0.2 mL of a 1M solution in tetrahydrofuran, 0.2 mmol). The solution was warmed to room temperature and quenched after 4 hours with saturated aqueous sodium bicarbonate. The mixture was extracted with ethyl acetate and the combined organic extracted washed with brine, dried (MgSO₄), and concentrated. Purification by radial chromatography (SiO₂, 5% MeOH in CH₂Cl₂) gave 22 mg (73%) of the desired product as a yellow solid: 1H NMR (acetone-d6) 7.40 (d, J=8.0 Hz, 2H), 7.31 (d, J=7.0 Hz, 1H), 6.89 (d, J=8.0 Hz, 2H), 6.81 (9, 1H), 6.42 (dd, J=8.0, 2.5 Hz, 1H), 6.20 (s, 1H), 4.15 (t, J=6.0 Hz, 3H), 2.95 (M, 1H), 2.80 (t, J=6.0 Hz, 2H), 2.50–2.60 (m, 6H), 2.20 (m, 2H), 1.20–1.80 (16H).

TEST PROCEDURE

General Preparation Procedure

In the examples illustrating the methods of the present invention, a post-menopausal model was used in which effects of different treatments upon circulating lipids were determined.

Seventy-five day old female Sprague Dawley rats (weight range of 200 to 225g) were obtained from Charles River Laboratories (Portage, MI). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-amino-phenazone in the presence of peroxidase to produce a p-quinone imine dye, which was read spectrophotemetrically at 500 nm. Cholesterol concentration was then calculated against a standard curve. The entire assay was automated using a Biomek Automated Workstation.

Uterine Eosinophil Peroxidase (EPO) Assay. Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the present invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the present invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the below data, estrogenicity also was assessed by evaluating the adverse response of eosinophil infiltration into the uterus. The compounds of the present invention did not cause any increase in the number of eosinophils observed in the stromal layer of ovariectomized rats, while estradiol cause a substantial, expected increase in eosinophil infiltration.

The data presented in the Tables 1 below reflects the response of 5 to 6 rats per treatment.

TABLE 1

| Compound | Dose mg/kg | Uterine Weight (% increase vs. OVX) | Uterine EPO (V. max) | Serum Cholesterol (% decrease vs. OVX) |
|---|---|---|---|---|
| $EE_2$ | 0.1 | 86.3 | 116.4 | 81.4 |
| Example 1 | 0.1 | -3.3 | 6.6 | 20.3 |
|  | 1.0 | 3.0 | 12.0 | 23.1 |
|  | 10.0 | 60.2 | 12.0 | 38.6 |
| Example 2 | 0.1 | 32.0 | 4.8 | 57.8 |
|  | 1.0 | 17.1 | 4.8 | 71.8 |
|  | 10.0 | 6.7 | 3.6 | 34.9 |
| Example 4 | 0.1 | 32.0 | 2.1 | 65.5 |
|  | 1.0 | 30.7 | 8.1 | 56.6 |
|  | 10.0 | 24.2 | 10.6 | 58.3 |
| Example 5 | 0.1 | 21.2 | 21.2 | 77.6 |
|  | 1.0 | 10.4 | 4.2 | 76.3 |
|  | 10.0 | 6.4 | 5.3 | 65.8 |
| Example 6 | 0.1 | 65.7 | 17.7 | 57.4 |
|  | 1.0 | 22.8 | 4.2 | 46.8 |
|  | 10.0 | 22.0 | 4.5 | 63.9 |

In addition to the demonstrated benefits of the compounds of the present invention, especially when compared 5 to estradiol, the above data clearly demonstrate that compounds of Formula I are not estrogen mimetics. Furthermore, no deleterious toxicological effects (survival) were observed with any treatment.

Osteoporosis Test Procedure

Following the General Preparation Procedure, infra, the rats were treated daily for 35 days (6 rats per treatment group) and sacrificed by carbon dioxide asphyxiation on the 36th day. The 35 day time period was sufficient to allow maximal reduction in bone density, measured as described herein. At the time of sacrifice, the uteri were removed, dissected free of extraneous tissue, and the fluid contents were expelled before determination of wet weight in order to confirm estrogen deficiency associated with complete ovariectomy. Uterine weight was routinely reduced about 75% in response to ovariectomy. The uteri were then placed in 10% neutral buffered formalin to allow for subsequent histological analysis.

The right femurs were excised and digitilized x-rays generated and analyzed by an image analysis program (NIH image) at the distal metaphysis. The proximal aspect of the tibiae from these animals were also scanned by quantitative computed tomography.

In accordance with the above procedures, compounds of the present invention and ethynyl estradiol ($EE_2$) in 20% hydroxypropyl β-cyclodextrin were orally administered to test animals. Proximal tibiae metaphysis data presented in Table 2 are the results of formula I compound treatments compared to intact and ovariectomized test animals. Results are reported as percent protection against bone loss which was calculated for individual animals by the following formula: % protection=$(BMD_{test}BMD_{ovx})/(BMD_{sham}-BMD_{ovx})\times 100$.

TABLE 2

| Compound/Treatment | Dose/kg | Tibia BMD pQCT (% protection) |
| --- | --- | --- |
| EE2 | 0.1 mg | 60.9* |
| Example 6 | 0.01 mg | 23.1 |
|  | 0.1 mg | 52.6* |
|  | 1.0 mg | 30.1 |
|  | 3.0 mg | 59.6* |

*P <= 0.5 two tailed Student's T Test on raw data.

In summary, ovariectomy of the test animals caused a significant reduction in tibae density compared to intact, vehicle treated controls. Orally administered ethynyl estradiol ($EE_2$) prevented this loss, but the risk of uterine stimulation with this treatment is ever-present.

The compounds of the present invention also prevented bone loss in a general, dose-dependent manner. Accordingly, the compounds of the present invention are useful for the treatment of post-menopausal syndrome, particularly osteoporosis.

MCF-7 Proliferation Assay MCF-7 breast adenocarcinoma cells (ATCC HTB 22) were maintained in MEM (minimal essential medium, phenol red- free, Sigma, St. Louis, Mo.) supplimented with 10% fetal bovine serum (FBS) (V/V), L-glutamine (2 mM), sodium pyruvate (1 mM), HEPES {(N-[2-hydroxyethyl]piperazine-N'-[2-ethanesulfonic acid] 10 mM}, non-essential amino acids and bovine insulin (1 ug/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium (Ca++/Mg++free HBSS (phenol red-free) supplemented with 10 mM HEPES and 2 mM EDTA). Cells were washed twice with assay medium and adjusted to 80,000 cells/mL. Approximately 100 µL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 µL transferred to triplicate microcultures followed by 50 µL assay medium for a final volume of 200 µL. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallac BetaPlace β counter. Results in Table 4 below show the $IC_{50}$ for certain compounds of the present invention.

TABLE 3

| Compound (Example Reference) | $IC_{50}$ nM |
| --- | --- |
| 1 | 10.0 |
| 2 | 1.0 |
| 5 | 10.0 |
| 6 | 0.6 |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenz[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

Uterine Fibrosis Test Procedures

Test 1

Between 3 and 20 women having uterine fibrosis are administered a compound of the present invention. The amount of compound administered is from 0.1 to 1000 mg/day, and the period of administration is 3 months.

The women are observed during the period of administration, and up to 3 months after discontinuance of administration, for effects on uterine fibrosis.

Test 2

The same procedure is used as in Test 1, except the period of administration is 6 months.

Test 3

The same procedure is used as in Test 1, except the period of administration is 1 year.

Test 4

A. Induction of fibroid tumors in guinea pig.

Prolonged estrogen stimulation is used to induce leiomyomata in sexually mature female guinea pigs. Animals are dosed with estradiol 3–5 times per week by injection for 2–4 months or until tumors arise. Treatments consisting of a compound of the invention or vehicle is administered daily for 3–16 weeks and then animals are sacrificed and the uteri harvested and analyzed for tumor regression.

B. Implantation of human uterine fibroid tissue in nude mice.

Tissue from human leiomyomas are implanted into the peritoneal cavity and or uterine myometrium of sexually mature, castrated, female, nude mice. Exogenous estrogen are supplied to induce growth of the explanted tissue. In some cases, the harvested tumor cells are cultured in vitro prior to implantation. Treatment consisting of a compound of the present invention or vehicle is supplied by gastric lavage on a daily basis for 3–16 weeks and implants are removed and measured for growth or regression. At the time of sacrifice, the uteri is harvested to assess the status of the organ.

Test 5

A. Tissue from human uterine fibroid tumors is harvested and maintained, in vitro, as primary nontransformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the present invention and vehicle. Levels of steroid hormone receptors are assessed weekly to determine whether important cell characteristics are maintained in vitro. Tissue from 5–25 patients are utilized.

Activity in at least one of the above tests indicates the compounds of the present invention are of potential in the treatment of uterine fibrosis.

Endometriosis Test Procedure

In Tests 1 and 2, effects of 14-day and 21-day administration of compounds of the present invention on the growth of explanted endometrial tissue can be examined.

Test 1

Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed.

On the day following surgery, animals in Groups 1 and 2 receive intraperitoneal injections of water for 14 days whereas animals in Group 3 receive intraperitoneal injections of 1.0 mg of a compound of the present invention per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2

Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow.

Approximately 50 days following surgery, animals assigned to Group 1 receive intraperitoneal injections of water for 21 days whereas animals in Group 2 receive intraperitoneal injections of 1.0 mg of a compound of the present invention per kilogram of body weight for the same duration. Following 21 days of treatment, each female is sacrificed and the endometrial explants and adrenals are removed and weighed. The explants are measured as an indication of growth. Estrous cycles are monitored.

Test 3

A. Surgical induction of endometriosis

Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

B. Implantation of human endometrial tissue in nude mice.

Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of a compound of the present invention supplied by gastric lavage on a daily basis for 3–16 weeks, and implants are removed and measured for growth or regression. At the time of sacrifice, the uteri is harvested to assess the status of the intact endometrium.

Test 4

A. Tissue from human endometrial lesions is harvested and maintained in vitro as primary nontransformed cultures.

Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, a compound of the invention, and vehicle. Levels of steroid hormone receptors are assessed weekly to determine whether important cell characteristics are maintained in vitro. Tissue from 5–25 patients is utilized.

Activity in any of the above assays indicates that the compounds of the present invention are useful in the treatment of endometriosis.

Inhibition of Aortal Smooth Cell Proliferation/Restenosis Test Procedure

Compounds of the present invention have capacity to inhibit aortal smooth cell proliferation. This can be demonstrated by using cultured smooth cells derived from rabbit aorta, proliferation being determined by the measurement of DNA synthesis. Cells are obtained by explant method as described in Ross, *J. of Cell Bio.* 50: 172 (1971). Cells are plated in 96 well microtiter plates for five days. The cultures become confluent and growth arrested. The cells are then transferred to Dulbecco's Modified Eagle's Medium (DMEM) containing 0.5–2% platelet poor plasma, 2 mM L-glutamine, 100 U/ml penicillin, 100 mg ml streptomycin, 1 mC/ml $^3$H-thymidine, 20 ng/ml platelet-derived growth factor, and varying concentrations of the present compounds. Stock solution of the compounds is prepared in dimethyl sulphoxide and then diluted to appropriate concentration (0.01–30 mM) in the above assay medium. Cells are then incubated at 37° C. for 24 hours under 5% $CO_2$/95% air. At the end of 24 hours, the cells are fixed in methanol. $^3$H thymidine incorporation in DNA is then determined by scintillation counting as described in Bonin, et al., *Exp. Cell Res.* 181: 475–482 (1989).

Inhibition of aortal smooth muscle cell proliferation by the compounds of the present invention are further demonstrated by determining their effects on exponentially growing cells. Smooth muscle cells from rabbit aortae are seeded in 12 well tissue culture plates in DMEM containing 10% fetal bovine serum, 2 mM L-glutamine, 100 U/ml penicillin, and 100 mg/ml streptomycin. After 24 hours, the cells are attached and the medium is replaced with DMEM containing 10% serum, 2 mM L-glutamine, 100 U/ml penicillin, 100 mg/ml streptomycin, and desired concentrations of the compounds. Cells are allowed to grow for four days. Cells are treated with trypsin and the number of cells in each culture is determined by counting using a ZM-Coulter counter.

Activity in the above tests indicates that the compounds of the present invention are of potential in the treatment of restenosis.

The present invention also provides a method of alleviating post-menopausal syndrome in women which comprises the aforementioned method using compounds of Formula I and further comprises administering to a woman an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 80 mg/day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation. The following formulation examples only are illustrative and are not intended to limit the scope of the present invention.

FORMULATIONS

In the formulations which follow, "active ingredient" means a compound of formula I, or a salt thereof.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5–1000 mg of active ingredient are made up as follows:

Formulation 3: Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 ml dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C, and transferred to a filling device. The required amount is then fed to a stainless steel container and diluted with the remaining propellant. The valve units are then fitted to the container.

Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 50 mg |
| Isotonic saline | 1,000 mL |

The solution of the above ingredients is intravenously administered to a patient at a rate of about 1 mL per minute.

Formulation 8: Combination Capsule I

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 9: Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 10: Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:

1. A compound of formula I

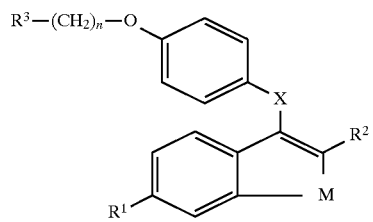

wherein $R^1$ is —H, —OH, —O($C_1$–$C_4$ alkyl), —OCOC$_6$H$_5$, —OCO($C_1$–$C_6$ alkyl), or —OSO$_2$($C_4$–$C_6$ alkyl);

$R^2$ is $C_1$–$C_6$ alkyl or $C_5$–$C_7$ cycloalkyl which is optionally substituted with 1 to 3 substitutents selected from the group consisting of $C_1$–$C_4$ alkyl, $C_1$–$C_4$ alkoxy, hydroxy, amino, nitro, and halo;

X is —CH(OH)— or —CH$_2$—;

M is —CH$_2$CH$_2$— or —CH=CH—;

n is 2 or 3; and $R^3$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt thereof.

2. A compound of claim 1 wherein n is 2, or a pharmaceutically acceptable salt thereof.

3. A compound of claim 1 wherein $R^3$ is 1-piperidinyl, or a pharmaceutically acceptable salt thereof.

4. A compound of claim 1 wherein $R^1$ is —OH, or a pharmaceutically salt thereof.

5. A compound of claim 1 wherein $R^1$ is —OCH$_3$, or a pharmaceutically acceptable salt thereof.

6. A compound of claim 1 wherein $R^2$ is $C_1$–$C_6$ alkyl, or a pharmaceutically acceptable salt thereof.

7. A compound of claim 1 wherein $R^2$ is ethyl, or a pharmaceutically acceptable salt thereof.

8. A compound of claim 1 wherein $R^2$ is hexyl, or a pharmaceutically acceptable salt thereof.

9. A compound of claim 1 wherein $R^2$ is $C_5$–$C_7$ cycloalkyl which is optionally substituted with 1 to 3 substituents selected from the group consisting of $C_1$–$C_4$ alkyl, $C_1$–$C_4$ alkoxy, hydroxy, amino, nitro, and halo, or a pharmaceutically acceptable salt thereof.

10. A compound of claim 9 wherein $R^2$ is cyclohexyl, or a pharmaceutically salt thereof.

11. A compound of claim 9 wherein $R^2$ is 4-hydroxycyclohexyl, or a pharmaceutically acceptable salt thereof.

12. A compound of claim 1 wherein X is —CH(OH)—, or a pharmaceutically acceptable salt thereof.

13. A compound of claim 1 wherein X is —CH$_2$—, or a pharmaceutically acceptable salt thereof.

14. A compound of claim 1 wherein M is —CH$_2$—CH$_2$—, or a pharmaceutically acceptable salt thereof.

15. A compound of claim 14 wherein X is —CH$_2$—, or a pharmaceutically acceptable salt thereof.

16. A compound of claim 1 wherein M is —CH=CH—, or a pharmaceutically acceptable salt thereof.

17. A compound of claim 16 wherein X is —CH$_2$—, or a pharmaceutically acceptable salt thereof.

18. A compound of claim 1 wherein said salt thereof is the hydrochloride salt.

19. A pharmaceutical composition comprising a compound of claim 1, or a pharmaceutically acceptable salt thereof in combination with a pharmaceutically acceptable carrier, diluent, or excipient.

20. A method for alleviating the symptoms of post-menopausal syndrome comprising administering to a woman in need of such treatment an effective amount of a compound of claim 1, or a pharmaceutically acceptable salt thereof.

21. A method of claim 20 wherein said post-menopausal syndrome is osteoporosis.

22. A method of claim 20 wherein said post-menopausal syndrome is a cardiovascular disease.

23. A method of claim 22 wherein said cardiovascular disease is hyperlipidemia.

24. A method of claim 20 wherein said post-menopausal syndrome is estrogen-dependent cancer.

25. A method of claim 24 wherein said estrogen-dependent cancer is breast or uterine cancer.

26. A method for inhibiting uterine fibroid disease comprising administering to a woman in need of such treatment an effective amount of a compound of claim 1, or a pharmaceutically acceptable salt thereof.

27. A method for inhibiting endometriosis comprising administering to a woman in need of such treatment an effective amount of a compound of claim 1, or a pharmaceutically acceptable salt thereof.

28. A method for inhibiting aortal smooth muscle cell proliferation comprising administering to a woman in need of such treatment an effective amount of a compound of claim 1, or a pharmaceutically acceptable salt thereof.

29. A method for inhibiting restenosis comprising administering to a woman in need of such treatment an effective amount of a compound of claim 1, or a pharmaceutically acceptable salt thereof.

* * * * *